US010902523B2

(12) United States Patent
Rees

(10) Patent No.: US 10,902,523 B2
(45) Date of Patent: Jan. 26, 2021

(54) TRANSPLANTATION METHODS

(71) Applicant: Michael A. Rees, Maumee, OH (US)

(72) Inventor: Michael A. Rees, Maumee, OH (US)

( * ) Notice: Subject to any disclaimer, the term of this patent is extended or adjusted under 35 U.S.C. 154(b) by 1211 days.

(21) Appl. No.: 14/215,807

(22) Filed: Mar. 17, 2014

(65) Prior Publication Data

US 2014/0261468 A1    Sep. 18, 2014

Related U.S. Application Data

(60) Provisional application No. 61/788,222, filed on Mar. 15, 2013.

(51) Int. Cl.
*G06Q 40/08* (2012.01)
*G06Q 50/22* (2018.01)
*A61K 35/12* (2015.01)

(52) U.S. Cl.
CPC ............. *G06Q 40/08* (2013.01); *A61K 35/12* (2013.01); *G06Q 50/22* (2013.01)

(58) Field of Classification Search
CPC ........ G06Q 40/08; G06Q 50/00; G06Q 50/22; G06Q 10/00; A61K 35/12; G16H 20/40
See application file for complete search history.

(56) References Cited

U.S. PATENT DOCUMENTS

2005/0010449 A1 * 1/2005 Abukwedar ...................... 705/3
2011/0173023 A1    7/2011 Leclair et al.

FOREIGN PATENT DOCUMENTS

WO    2007058395 A1    5/2007

OTHER PUBLICATIONS

Segev et al. Kidney Paired Donation and Optimizing the Use of Live Donor Organs. JAMA, 2005. 293 (15): 1883-1890.*
Medicare (http://www.medicareinteractive.org/page2.php?topic=counselor&page=script&script_id=1744.) Accessed Jun. 22, 2015.*
American Kidney Fund_ http://www.kidneyfund.org/kidney-disease/esrd-treatment/paying-for-treatment/ Accessed Feb. 29, 2016.*
http://www.nytimes.com/2012/02/19/health/lives-forever-linked-through-kidney-transplant-chain-124.html?_r=0 Accessed Jul. 18, 2016.*
http://www.justsavelives.com/ Accessed Jul. 25, 2016.*
Rees et al. Call to develop a standard acquisition charge model for kidney paired donation. American Journal of Transplantation. Jun. 2012; 12(6):1392-7.*
Willis, HHS Issues Additional Guidance on Transitional Reinsurance Program. Brochure published Jan. 2013.*

(Continued)

*Primary Examiner* — Jerrah Edwards
*Assistant Examiner* — Rokhaya Diop
(74) *Attorney, Agent, or Firm* — Jacob M. Ward; Ward Law Office LLC

(57) ABSTRACT

Methods and systems are provided for transplantation of a biological material to a plurality of recipients from a plurality of donors. One or a series of paired donations are made, where one or more donors and/or recipients can be international in origin. Improved care and cost savings are obtained by shifting time-based burdens; i.e., dialysis versus transplantation. Additional transplants, including transplants involving international participants, results in the improvement of local and global healthcare.

28 Claims, 1 Drawing Sheet

(56) References Cited

OTHER PUBLICATIONS

Wallis et al. Kidney paired donation. Nephrol Dial Transplant (Jul. 1, 2011) vol. 26, No. 7, pp. 2091-2099, p. 2091, col. 2, para 1-2, col. 2 para 1, p. 2093, col. 1, para 2, p. 2094, col. 1, para 2, p. 2095, col. 1, para 1, col. 2, para 4, p. 2096, col. 2, para 3, Fig. 3A, 38.

Eberenz. Jewish Hospital Transplant Center Participates in First International Paired Kidney Exchange in America. KentuckyOne Health Jun. 1, 2012 (Jun. 1, 2012) [online]. [Retrieved on Sep. 26, 2014]. Retrieved from the internet <URL: http://www.jhsmh.org/About-Us/JHSMHNews-Center/News-Article/ID/1374/Jewish-Hospital-Transplant-Center-Participates-in-First-Internafional-Paired-Kidney-Exchange-in-America.aspx > Especially para 3-9.

Michael A Rees et al., "A Nonsimultaneous, Extended, Altruistic-Donor Chain," The New England Journal of Medicine, Mar. 12, 2009, pp. 1096-1101, vol. 360, No. 11.

\* cited by examiner

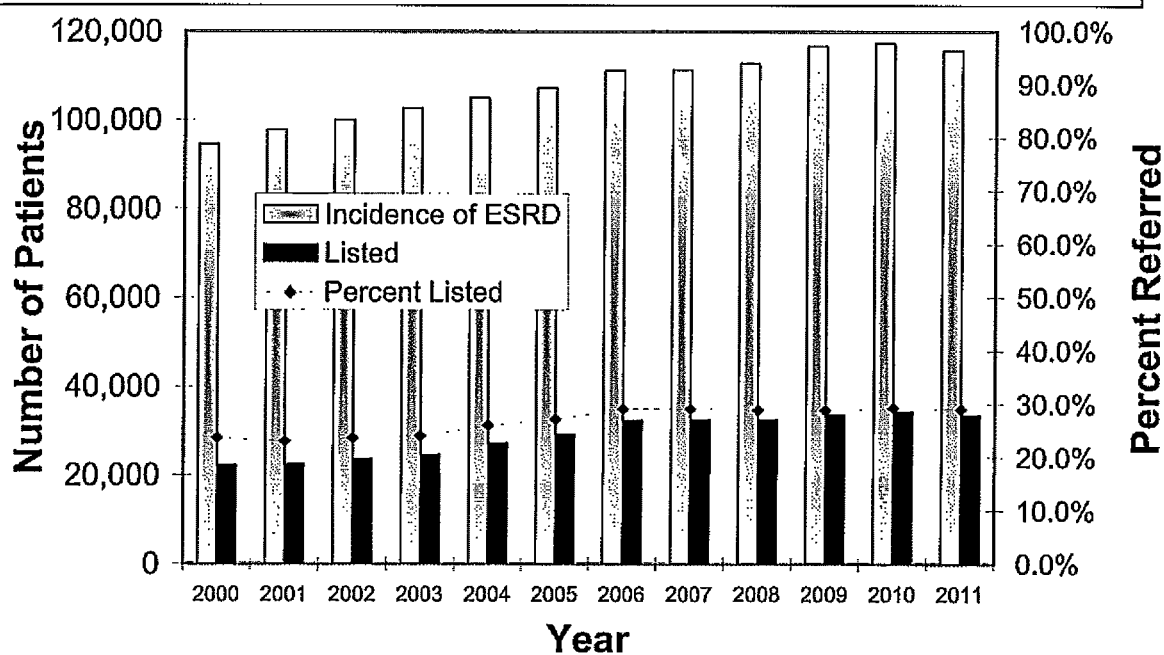

TRANSPLANTATION METHODS

CROSS-REFERENCE TO RELATED APPLICATIONS

This application claims the benefit of U.S. Provisional Application No. 61/788,222, filed on Mar. 15, 2013. The entire disclosure of the above application is incorporated herein by reference.

FIELD

The present technology relates to methods and systems for transplantation of biological material from a donor to a recipient, donor-recipient matching, and transplantation networks, particularly those involving kidney transplants.

INTRODUCTION

This section provides background information related to the present disclosure that is not necessarily prior art.

Transplantation of a biological material, such as a tissue or organ, from a donor to a recipient has become an important, and in certain cases, a routine practice to address medical issues relating to tissue and organ damage or failure, whether from injury or disease. For example, transplant organs can include heart, kidney, liver, lung, pancreas, intestine, and thymus, and transplant tissues can include musculoskeletal grafts such as bone and tendon, cornea, skin, heart valves, nerves, and veins. One transplant management concern relates to transplant rejection, where the recipient's body has an immune response to the transplanted biological material, which can lead to transplant failure. Accordingly, transplant rejection can be reduced through testing the prospective donor and recipient for matching based on antibodies, blood type, histocompatibility, and other factors to determine the most appropriate donor-recipient match. In certain cases, the use of immunosuppressants can mitigate transplant rejection. Finding and matching appropriate donors and recipients are therefore significant steps to increase the availability and utility of transplantation methods.

Taking kidney transplantation as one example, more than 100,000 patients with end-stage renal disease (ESRD) are currently on the waiting list in the United States for a deceased donor kidney transplant. Less than 11,000 of these patients will receive a deceased donor's kidney in 2014 and about 4,000 patients may die while waiting for a kidney. Another 2,500 will be removed from the waiting list because they may become too sick to be viable candidates for a transplant. Indeed, this is a growing problem since the length of the waiting list increases by about 7,000 patients every year. About 5,500 patients will receive a living donor's kidney in 2014, and over 500 of these will be the result of kidney exchanges or kidney paired donation (KPD).

Between 2000 and 2006, 166 kidney exchanges were performed in the United States and all of these were performed in simultaneous exchanges. The advent of non-simultaneous extended altruistic donor (NEAD) chains in 2007 revolutionized this nascent field as demonstrated by the performance of more than 2,400 kidney exchanges in the last 6 years—the majority as a result of NEAD chains. The importance of this increase in the number of living donor kidney transplants is emphasized by the fact that a deceased donor's kidney functions on average for 8.5 years before failing, whereas a living donor's kidney lasts an average of 16.5 years. Since kidney transplant recipients live more than 10 years longer than had they remained on dialysis, kidney exchanges are now producing more than 5,000 additional years of life annually.

When one considers the average annual cost of dialysis for one Medicare patient is $87,945 per year averaged over five years and compares this with the 5 year average annualized cost of $32,922 for transplantation, kidney exchanges have saved the U.S. healthcare system hundreds of millions of dollars. Assuming each living donor kidney transplant saves $100,000 (see Matas and Schnitzler, American Journal of Transplantation 2003; 4: 216-221 Payment for Living Donor (Vendor) Kidneys: A Cost-Effectiveness Analysis), kidney exchanges are now saving the U.S. healthcare system more than $50,000,000 annually.

There are approximately 2.5 million people worldwide receiving renal replacement therapy. Assuming three out of four of these people are in the developed world and one out of four are in the developing world, that leaves 625,000 people in the developing world on renal replacement therapy. Many individuals in the developing world do not have access to healthcare and are likely to die of renal failure without the opportunity for kidney transplantation or dialysis.

Providing increased opportunities for kidney transplantation, for example, could substantially improve the treatment, prognosis, and mitigate the costs associated with end stage renal disease across the globe. Even assuming that simply 1% of those in the developing world with renal disease would participate in a transplantation program, about 6,250 transplants could be performed. Given that there were 5,770 living donor kidney transplants in the United States in 2011, providing improved methods and systems relating to organ transplantation, donor matching, and transplantation networks could provide a significant increase in the number of U.S. and worldwide kidney transplants.

SUMMARY

The present technology includes methods and systems that relate to transplantation of a biological material from a donor to recipient. In particular, it is understood that the description of technology relating to kidney transplantation and kidney paired donation (KPD) made herein can be applicable to transplantation of a biological material in general, including transplantation of one or more various organs and tissues.

Methods for transplantation of a biological material are provided that include a pool of a plurality of donor-recipient pairs, each donor-recipient pair including a recipient in need of the biological material and a donor willing to provide the biological material to the recipient. A first biological material is transplanted from a first donor to a first recipient, where the first donor and the first recipient are not from the same donor-recipient pair, and the first recipient overcomes a first barrier. A second biological material is transplanted from a second donor to a second recipient, where the second donor and the second recipient are not from the same donor-recipient pair, and the second recipient overcomes a second barrier.

One or both of the first barrier and the second barrier can include an antibody against a human leukocyte antigen (HLA) antigen, an antibody linked to organ rejection, a blood type incompatibility, a physiological barrier, a viral incompatibility, a lower prognosis overcome by an improved transplantation match, a transplantation match incompatibility that can be overcome by desensitization, a financial barrier, and combinations thereof. Examples of a physiological barrier include a size difference between a proposed donor and a recipient. Examples of viral incompatibility include cytomegalovirus (CMV) and Epstein-Barr virus (EBV). In a certain embodiment, the first barrier includes a member selected from the group consisting of: an antibody against an HLA antigen, another antibody linked to organ rejection, a blood type incompatibility, a physiological barrier, a viral incompatibility, a lower prognosis overcome by an improved transplantation match, a transplantation match incompatibility that can be overcome by desensitization, and combinations thereof, and the second barrier includes a financial barrier.

Other methods for transplantation of a biological material to a plurality of recipients from a plurality of donors are provided. A first biological material is transplanted from a first donor to the first recipient, where the transplanting occurs within a first nation. A second biological material is transplanted from a second donor to a second recipient. The first recipient is a citizen of the first nation and the first donor, the second donor, and second recipient are not citizens of the first nation.

Systems for transplantation of a biological material to a plurality of recipients from a plurality of donors are provided. The systems include a first transplant center, a health insurance provider, and a transplant partner. The first transplant center is operable to perform transplantation of the biological material. The health insurance provider is responsible for health care costs for a first recipient. The transplant partner is operable to identify a paired donation between a portion of the recipients and a portion of the donors, where the portion of recipients includes the first recipient. The transplant partner offsets a transplant cost for a second recipient based on a reduction in a projected cost of care over a period of time following transplantation of the first recipient. At least a portion of an amount based on the reduction in the projected cost of care is provided to the transplant partner from the health insurance provider.

The present technology redesigns the referral and management of end stage renal disease (ESRD) patients for renal transplantation and capitalizes on the fact that in some countries dialysis costs more than twice the cost of renal transplantation (i.e. 2013 USRDS Annual Report average dialysis annual cost is $87,945 whereas average annual renal transplantation cost is $32,922), so that creating more kidney transplants by improved referral and management of ESRD patients creates significant savings that can be converted into revenue for a business focused on selling reinsurance for ESRD patients for a fixed price and then providing healthcare for these ESRD patients at a cost less than the fixed price.

Aspects of the present technology include reverse transplant tourism, which identifies indigent patients with kidney failure and their willing living donor(s) whose barrier to transplantation is poverty and pairs these patients with insured patients who live in countries where the cost of dialysis exceeds the cost of kidney transplantation such that paying for two transplants is less expensive than paying for the dialysis of one patient, so that the indigent donor gives their kidney to the insured patient in exchange for the indigent donor's paired patient receiving a kidney transplant and necessary immunosuppressive medications.

In certain cases, reverse transplant tourism is combined with the redesign of referral and management of ESRD patients to provide the capital to fund reverse transplant tourism without having to involve the insured patient's original insurance provider and simultaneously provides a greater revenue stream to the ESRD reinsurance business.

Further areas of applicability will become apparent from the description provided herein. The description and specific examples in this summary are intended for purposes of illustration only and are not intended to limit the scope of the present disclosure.

DRAWINGS

The drawing described herein is for illustrative purposes only and is not intended to limit the scope of the present disclosure.

The FIGURE graphically depicts the percentage of patients referred for renal transplantation between 2000 and 2011.

DETAILED DESCRIPTION

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description are to be understood as modified by the word "about" in describing the broadest scope of the technology.

The present technology relates to the methods and systems for transplantation of a biological material, donor matching of the biological material, and transplantation networks for the biological material. The methods and systems provide ways to address certain issues surrounding the transplantation process, including improving successful outcomes of transplantation procedures and mitigating financial burdens related thereto. In particular, the present methods and systems are directed to transplantation of a biological material from a donor to recipient, where the biological material can include an organ or tissue. It is understood that the description of technology made herein relating to kidney transplantation and kidney paired donation (KPD) is applicable to the transplantation of various biological materials, including one or more various organs and tissues. Details of the present technology follow with particular reference to kidney transplantation, diseases related to kidney failure, including end stage renal disease (ESRD), but the present technology is not expressly limited thereto.

Methods and Systems to Reduce the Failure Rate of Kidney Paired Donation Matches that Simultaneously Evaluate Multiple Possibilities Instead of Finding a Single Optimized Solution.

The present methods and systems allow for the simultaneous identification and evaluation of multiple possible living donor and kidney failure recipient combinations for the purpose of kidney paired donation (KPD) matching that can lead to a higher rate of conversion of a possible match to a completed transplant. KPD matches one incompatible donor/recipient pair to another donor/recipient pair in the same situation, so that the donor of the first pair gives to the recipient of the second, and vice versa. In other words, the two donor/recipient pairs exchange donor kidneys so that each recipient receives a more compatible kidney than would be obtained from their original donor.

A First Generation Matching Process

A first generation matching process was developed to match patients for the purpose of KPD. The first generation matching process found potential 2-way exchanges, assigned a point value to each potential 2-way exchange, and then rank-ordered the possible exchanges such that the highest scoring 2-way exchange was at the top and the lowest scoring exchange was at the bottom. Exchanges were then chosen giving preference to the highest scoring exchanges. The first generation matching process could be implemented on a single workstation, for example, and was able to output files that could be shared across a network, such as the internet, or could be used as a web-based application.

The first generation matching process was modified, taking into account that optimization of matches was a better approach for kidney-paired donation than rank ordering. It also appeared that 2-way exchanges did not allow as many exchanges as would be found by a matching process that could identify exchanges for more than two pairs to participate in a single exchange. Accordingly, the first generation matching process was modified so that it was web-based in that it allowed transplant centers in different locations to access a single database. It allowed for entry of the required data elements into that database from distant workstations linked over the internet to a centralized server. It created a compatibility matrix of all participating donors and recipients and created a matrix recording the point score of individual, compatible donor and recipient combinations. It utilized these two matrices to perform and optimize a match run that identified the best single solution of mutually exclusive kidney exchanges from amongst the myriad possible solutions available. It provided a single solution that allowed for one of two aims to be optimized: (1) total number of KPD transplants or (2) total quality of transplants achieved as measured by a point score developed by expert opinion of the Scientific Operation Committee of the Alliance for Paired Donation. In addition, eight optimized solutions were identified, four based on quantity of transplants and four based on quality of transplants. Limiting the maximum number of transplants to 2 or 3 or 4 or unlimited transplants per chain or exchange identified the four solutions for each aim.

The first generation matching process was further modified to add the possibility of identifying non-simultaneous, extended altruistic donor KNEAD) chains as part of the optimized, mutually exclusive solution. Using this modified first generation matching process, the nonprofit organization The Alliance for Paired Donation, Inc. identified and reduced to practice the first NEAD chain and described this work in a publication in the New England Journal of Medicine in March 2009. The Alliance for Paired Donation, Inc. (APD) utilized this software to identify and convert to KPD transplants all the KPD transplants performed through the APD. During this period of time, the failure rate of converting identified optimized matches to completed KPD transplants was 87%.

Several reasons for failure to proceed to a completed KPD transplant were identified and quantified. One class of failures was associated with the participating hospital providing data that failed to predict truly compatible combinations when evaluated with actual donor and recipient blood samples using a crosshatch test. A second class of failures resulted from transplant centers rejecting donors that the APD offered to their recipients, citing center-specific clinical contraindications that could have been identified and recorded as preferences. These preferences would allow such combinations to be avoided, thus creating a more accurate compatibility matrix in which immunologically acceptable, but clinically unacceptable combinations, would not be identified as compatible in the first place. Based on these observations, the APD software was modified to allow for: 1) improved blood test compatibility data collection, 2) more sophisticated centralized laboratory tracking of blood samples and crosshatch results, and 3) a mechanism to have participating transplant centers record center-specific clinical preferences for acceptable donors. These changes lead to the creation of an improved compatibility matrix from which an optimized solution could be generated. Transplant offers could then be prepared by APD staff and offered to participating centers via email or phone.

These changes improved the conversion rate from identified plausible KPD donor and recipient matches to completed KPD transplants. Even so, the failure rate remained unacceptably high. Further improvements therefore had the potential to identify the maximum number or quality of KPD transplants. Likewise, it appeared that the best approach was to identify the single best optimized solution (the combination of 2-, 3-, 4- or longer chains and exchanges that were mutually exclusive in terms of the donor and recipients comprising the solution) and work through it until it failed or resulted in completed KPD transplants. It was clear that reducing the time from identifying an optimal solution until either proving it was not viable or the transplants were completed was a laudable goal. Otherwise, an alternative strategy was not clearly evident. As evidence that an alternative approach was not available, there were three national KPD programs in existence at this time (National Kidney Registry, APD, and the United Network for Organ Sharing KPD program) and several multi-center or single center programs all of which utilized software that found a single best match or a single best amalgamation of matches in a single best solution. No one had suggested an alternative approach. Understanding the limitations of the first generation matching process described above, and appreciating the redesigned second generation matching process described below, makes clear the advantages of the second generation matching process over the first generation matching process and how the second generation matching process is distinguished therefrom.

A Second Generation Matching Process

The second generation matching process of the present technology includes altering the matching process from identifying a single optimized solution in which the components of that solution were followed through to either failure or completed transplants, to an alternative process designed to identify the single 1-way combinations most likely to be incorporated into a large number of the top scoring optimized solutions. A 1-way combination identifies a compatible match between a single donor from one donor/recipient pair in the KPD pool, matched with a single recipient from another donor/recipient pair. It turned out that the while there were enormously large numbers of possible solutions, the number of 1-way combinations that comprised those solutions very close to the best solution, was only about 2-3 times larger than the total number of 1-way combinations involved in the single best optimized solution.

Thus, the second generation matching process identifies all of the 1-way combinations that could be involved in the top-scoring solutions optimized for either quality or quantity and offers these potential 1-way combinations to the HLA laboratories and clinical teams of the participating transplant centers. Accordingly, instead of identifying and offering a single optimized and mutually exclusive solution, a limited number of competing 1-way combinations can be offered that might comprise an optimized solution—if only the compatibility matrix could be made more accurate. These 1-way combinations, which may comprise the optimized solution, could be vetted simultaneously by the participating transplant centers and the APD Centralized Laboratory, to therefore determine if each 1-way combination was truly compatible by blood testing and if the donors were truly acceptable to the transplant center clinical teams. After vetting these many combinations, the revised compatibility matrix would become more accurate and more likely to result in the identification of a single optimized and mutually exclusive solution that proceeds to completed transplants. In addition, instead of overburdening transplant centers by having them evaluate every possible 1-way combination identified from the entire KPD pool of donor/recipient pairs, the process would limit the workload of participating transplant centers by focusing only on those 1-way combinations most likely to be utilized in an optimized solution.

If the first generation matching process took two weeks to evaluate the component combinations comprising a single optimized and mutually exclusive solution, and 8 out of 10 solutions failed to convert to completed transplants, then it would take 4 months to sequentially evaluate 8 optimized solutions and would likely leave a trail of partially completed pieces of former optimized solutions—that in the end were not truly optimized. In the second generation matching process, thousands of possible optimized solutions could be vetted simultaneously by the identification of the pool of 1-way combinations predicted to be involved in these solutions and thus most likely to be involved in the ultimate single optimized solution capable of culminating in completed KPD transplants. Instead of vetting each solution one-at-a-time, in a sequential, iterative fashion, in an effort to modify the compatibility matrix to reflect reality, those 1-way combinations that would have taken 4 months to evaluate in the old process can now be identified simultaneously and vetted over a much shorter time period to identify the 1-way combinations most likely to be involved in the single best and mutually exclusive solution leading to completed transplants. By performing not one match run, but two, now utilizing an exploratory match run to identify those 1-way combinations that could be part of the solution that would actually lead to completed transplants, those possible 1-way combinations can be identified, vetted in a short period of time, and used to generated an improved compatibility matrix. With a more accurate compatibility matrix, a more robust optimized and mutually exclusive solution can be identified by a final match run that is more likely to lead to completed KPD transplants. The second generation matching process allows for the simultaneous identification and evaluation of multiple possible living donor and kidney failure recipient combinations for the purpose of kidney paired donation (KPD) matching that leads to a higher rate of conversion of a possible match to a completed transplant.

Identification of Costs and Strategies to Reduce Costs in Complex Medical Conditions for Healthcare Organizations and Monetizing the Process to Incentivize Cost Savings Infrequent, but extremely expensive medical conditions, including transplantation of a biological material, comprise a significant portion of overall healthcare costs. In many cases, there is little opportunity for cost reduction in the treatment of these complex medical conditions. However, when that opportunity arises, it can provide a significant savings—especially as a proportion of the total savings possible from various interventions under consideration. The difficulty is to identify which conditions represent the best return on investment. The present methods and systems identify a population of patients with end stage renal failure and redirect their treatment approach to allow for early kidney transplantation instead of prolonged dialysis. In so doing, significant savings are achieved, the number of successful transplantations is increased, and the overall wellbeing of a patient population is improved.

Donor Complication Insurance to Protect a Recipient Hospital in a Kidney Paired Donation Transplant The present technology includes methods and systems that use financial and insurance models to allow participating transplant programs in a paired exchange pool to build catastrophic insurance for the expenses associated with a donor complication into the cost of carrying out such transplants.

Living donor kidney transplantation began with one transplant center acting as the hospital for both the donor and recipient. This hospital assumed the financial responsibility for both the donor and the recipient. With time, Medicare built a system for donor complications that stated that the recipient's insurance company was responsible for complications related to that recipient's donor. When one transplant center was responsible for both the donor and the recipient, this system worked well. If that center caused a donor complication, then they were responsible for taking care of the complication and passing those expenses onto the recipient's insurance company. When the recipient's insurance company was Medicare, this made the process simple because the transplant center only had to put these donor complication expenses onto their cost report. When the recipient had a commercial insurer, it became more of a negotiated settlement as to who should be responsible for the expenses and for how much. In general, the recipient's insurance company has paid for complications for three months after the donation, but there have not been hard and fast rules concerning such situations.

With the advent of KPD, the living donor's kidney can be shipped from one transplant center to another. In so doing, the living donor donating the kidney and the recipient receiving the kidney are not at the same transplant center. In fact, the recipient's transplant center has to pay the donor center for the cost of removing the living donor's kidney. In addition, the recipient's transplant center now bears the risk of financial responsibility for any complication that occurs to the donor, a risk of financial responsibility that is completely out of their control.

As one working example, the recipient's transplant center can contract with the donor's hospital so that the recipient's hospital agrees to pay the donor's hospital 70% of charges for the donor nephrectomy and associated hospital expenses. If everything goes as planned and the total donor charges are $25,000, then the recipient hospital will have to pay the donor's hospital $17,500—a reasonable amount to pay for these services. But imagine a situation where the donor has a catastrophic complication and is in the hospital for 6 months and the total charges are $1,000,000. Now the recipient's hospital has to pay $700,000. If the recipient's hospital tries to pass these expenses on to the recipient's insurance company, they refuse to pay more than for the first 3 months as specified in their contract, so now the recipient's hospital has to pay the donor hospital 70% of charge for a complication that they did not cause and cannot control the costs by taking care of the patient at their own hospital. Not only can they not control the cost, but now they have to pay the donor's hospital for the services they are providing at a rate that is actually profitable for the donor hospital that caused the complication in the first place. Amazingly enough, this construct is actually enforced by the current Medicare regulations, built prior to the advent of KPD, that dictate that the complications related to a living donor must be passed through to the recipient's hospital.

The present technology provides a new process to deal with this problem of donor complications in a kidney paired exchange with shipped kidneys. The process allows an insurance company to underwrite this risk and allows all the participating hospitals in a paired exchange pool to pay their appropriate portion of the premium with each transplant they perform. Then, if there is a catastrophic donor complication, the insurance policy would pay for the expenses rather than the recipient's hospital. For example, let's say an insurance company underwrites the risk of a donor complication at 1 major complication every 1,000 transplants and estimates the expense for this at $1,000,000. Let's say the insurance company then charges $2,000 per transplant to cover this risk. So every year the transplant centers in the kidney paired donation pool include an additional $2,000 per transplant for this donor complication insurance policy. Assume 200 kidney paired donation transplants occur per year and that 3 years go by before the first major donor complication. After three years, the insurance company would have collected $2,000×600 transplants or $1.2M and thus would have enough money to pay for the expenses related to the catastrophic donor complication that occurred 3 years into the program.

Combining Kidney Paired Donation and Desensitization Allows for the Transplantation of End Stage Renal Transplant Patients that Cannot be Transplanted by Either Option Alone Desensitization is a strategy whereby patients with unacceptable donor-specific antibodies are treated with plasmapheresis to remove these antibodies and/or treated with intravenous immunoglobulin infusion to keep these antibodies from returning and causing rejection. If successful, desensitization allows patients to be transplanted with their original intended donor despite the initial presence of donor-specific antibodies. For those patient with very high levels of donor-specific antibodies (especially to HLA class ii antigens), desensitization is not an appropriate treatment strategy given the high failure rate. Kidney paired donation is a strategy that aims to avoid transplantation in the face of donor-specific antibodies, by allowing incompatible donor and recipient pairs to exchange their incompatible donor's kidney in order to find a living donor kidney against which they do not have preformed donor-specific antibodies. Sometimes the characteristics of the donor and/or recipient make it highly unlikely that a compatible donor will be identified through kidney paired donation. In these cases, and in those cases where desensitization is not likely to succeed, a combination of kidney paired donation and desensitization can be used to find a donor against whom the recipient still has donor-specific antibodies, but now these donor-specific antibodies are more amenable to desensitization. The present process involves bringing together an organization with expertise in kidney paired donation with an organization with expertise in desensitization so that transplant centers can be offered both of these options from a single provider. In present process, the second generation matching process and expertise in desensitization are merged together and offered as a single service.

International Kidney Paired Donation as a Means to Recruit International Patients to the United States This is a method in which kidney paired donation (KPD) services, including a matching process, such as the second generation matching process, is provided to a country to run its national kidney paired donation program with the expectation that some of the incompatible donor and recipient pairs will not be found matches, that the country will be willing to enroll those unmatched patients in an international paired donation program, and that some of these patients will be found matches with pairs from the U.S. and thus travel to the U.S. for their kidney transplants. Given the reality that on an annual basis less than half of the patients enrolled in a KPD program will be successfully matched and transplanted, it is likely that one or more international countries using the same KPD matching process will be willing to pool together their unmatched, incompatible pairs in order to find additional opportunities for compatible living donor kidney transplantation through international KPD.

To date, only a few international kidney paired exchanges have been performed. However, it is clear to the transplant community that international kidney paired donation could increase the total number of living donor kidney transplants performed. What is less clear is where these transplants will be performed. Transplant professionals who consider international KPD expect that all of the transplants will be performed in the patient's native country. The present technology accounts for the scenario where other countries will allow their patients to travel to the United States for transplantation and they will pay U.S. transplant centers to perform these renal transplants. The cost of dialysis is so expensive that paying for U.S. transplant centers to perform renal transplants remains less expensive in the long run than continuing to pay for dialysis in the patient's home country. In addition, U.S. law currently demands that living donor kidneys transplanted by U.S. transplant centers must undergo nephrectomy by an organ procurement and transplantation network (OPTN)-approved program. As the only OPTN-approved programs are within U.S. borders, any international donor's kidney transplanted into a U.S. recipient must be removed by a U.S. transplant center. Thus, international donors can travel to the U.S. to have their kidney removed and many will be willing to do this given the reputation of the U.S. as a world leader in healthcare. In contrast, most U.S. donors may be unwilling to travel abroad to have their kidney removed. Thus, it is more likely that the international recipient will travel to the U.S. for their transplant and, at least for patients traveling from European countries with socialized medicine, this will mean that the government will be paying for their kidney transplant. By providing web-based matching processes to countries to help them identify potential KPD matches from pools of incompatible pairs within their country, one creates an opportunity to facilitate the entry of the unmatched pairs into a larger, international pool of such patients and donors. In so doing, a greater opportunity to find international exchanges exists and thus the opportunity to recruit such pairs to travel to the U.S. By traveling to the U.S. for transplantation, more Americans will be transplanted and U.S. transplant centers will financially benefit as a result of a higher kidney transplantation volume.

Redesigning Referral of End Stage Renal Disease Patients for Renal Transplantation Kidney failure affects over 600,000 Americans and consumes 6.3% of the entire Medicare budget at an annual cost of over $34 Billion. The present technology offers two new approaches to improve access to living donor kidney transplantation—the treatment proven to not only provide the best quality of care in terms of patient survival and quality of life, but also proven to be the least expensive treatment for end stage renal disease (ESRD) patients. The present methods and systems redesign the renal transplantation referral process of patients with ESRD to increase the number of patients referred, evaluated, and successfully transplanted. An important relationship in this process is between what is referred to herein as a transplant partner (TP) and a health insurance provider (HIP). The HIP can be an insurance company, a self-insured company, or a government provider such as Medicare or Medicaid. The TP can be one of various organizations or business forms, including nonprofit and for-profit entities, that serves to coordinate the transplantation methods and systems as further described below. In certain embodiments, the TP can provide re-insurance, consultation, and/or be a part of the HIP. For example, where the TP provides re-insurance, the HIP purchases risk from the TP, or put another way, the HIP sells risk to the TP, where the TP then provides the cost of health care for one or more transplants to a transplant center.

It is presupposed that the HIP will agree, with appropriate security measures in place, to release protected health information (PHI) to the transplant partner (TP). To illustrate, a target population can include all HIP-covered lives within a chosen geographic area providing a minimum of 1,000,000 lives. Using southern California as an example, where the incidence of ESRD is 389 new patients per year, it is expected about 389 ESRD patients would therefore be identified. Commercial HIPs are responsible for providing 33 months of health insurance coverage for a patient diagnosed with ESRD prior to Medicare assuming financial responsibility. Current estimations are that commercial HIPs pay about $500,000 for 33 months of dialysis and $200,000 for patients undergoing preemptive renal transplantation—thus providing the opportunity to save up to $300,000 per ESRD patient more effectively managed. Once established, the TP can offer reinsurance to existing HIPs to cover those patients who develop ESRD. The TP can estimate the expected savings, sell the reinsurance at a rate that is sufficiently below the insurers current costs so that the transaction is attractive to the HIP. The TP can then manage the HIP's ESRD patients to ensure timely referral for renal transplantation to transplant centers with short waiting times and identify and rapidly implement all living donor transplantation opportunities.

Financial Impact of End Stage Renal Disease

According to the 2013 U.S. Renal Data Systems (USRDS) Annual Report, there were 615,899 patients treated for end-stage renal disease (ESRD) in the U.S. at the end of 2011. Of those, 430,273 patients were being treated by dialysis and 185,626 had a functioning transplant. Medicare spent $34.4 billion to care for these patients or 6.3 percent of all Medicare spending, which reached $549 billion in 2011. When non-Medicare spending is factored in, total ESRD costs reached $49.3 billion or 1.8% of the $2.7 trillion the United States spent on healthcare in 2011. Thus, costs related to ESRD represent one of the largest categories of Medicare expenses, costing $87,945 per year for each patient treated with hemodialysis. While transplantation costs more than dialysis in the first year, when averaged over the life of the transplant, kidney transplantation costs $32,922 per patient per year, saving Medicare $275,115 per patient over five years compared with hemodialysis (see Table 1).

TABLE 1

Savings to Medicare from Renal Transplantation versus Dialysis

| Number of transplants | Cost of Dialysis | Years of survival on dialysis | Total cost of dialysis | Cost first year of transplant | Cost years 2-10 of transplant | Years of cost to Medicare | Total cost of transplant | Savings to Medicare |
|---|---|---|---|---|---|---|---|---|
| 1 | 87,945 | 5 | 439,725 | 100,000 | 32,922 | 5 | 164,610 | 275,115 |
| 10 | 87,945 | 5 | 4,397,250 | 100,000 | 32,922 | 5 | 1,646,100 | 2,751,150 |
| 25 | 87,945 | 5 | 10,993,125 | 100,000 | 32,922 | 5 | 4,115,250 | 6,877,875 |
| 50 | 87,945 | 5 | 21,986,250 | 100,000 | 32,922 | 5 | 8,230,500 | 13,755,750 |
| 100 | 87,945 | 5 | 43,972,500 | 100,000 | 32,922 | 5 | 16,461,000 | 27,511,500 |
| 250 | 87,945 | 5 | 109,931,250 | 100,000 | 32,922 | 5 | 41,152,500 | 68,778,750 |
| 500 | 87,945 | 5 | 219,862,500 | 100,000 | 32,922 | 5 | 82,305,000 | 137,557,500 |
| 1000 | 87,945 | 5 | 439,725,000 | 100,000 | 32,922 | 5 | 164,610,000 | 275,115,000 |
| 1500 | 87,945 | 5 | 659,587,500 | 100,000 | 32,922 | 5 | 246,915,000 | 412,672,500 |
| 2000 | 87,945 | 5 | 879,450,000 | 100,000 | 32,922 | 5 | 329,220,000 | 550,230,000 |
| 2500 | 87,945 | 5 | 1,099,312,500 | 100,000 | 32,922 | 5 | 411,525,000 | 687,787,500 |
| 3000 | 87,945 | 5 | 1,319,175,000 | 100,000 | 32,922 | 5 | 493,830,000 | 825,345,000 |

Despite the opportunity for cost savings and added value, the principal stakeholders—Medicare, commercial insurance carriers, and transplant hospitals—have been reluctant to make the investment necessary to improve the overall management of ESRD. None of these stakeholders has been willing to invest resources to realize healthcare cost savings over several years. Consider the commercial insurance company business model. Commercial HIPs generate revenue by having actuaries estimate the expected total cost for providing healthcare to a given population. A profit margin is then added and underwriters build insurance policies designed to sell to the expected number of customers so that the revenue generated covers both the cost of healthcare provided and the profit margin. If the insurance company wants more revenue, the model is not to try to save money by outperforming the actuarial prediction, but rather to sell more policies. The commercial HIP business model does not currently generate revenue by realizing healthcare cost savings over several years. Rather, commercial HIPs make money by accurate prediction of total cost, appropriate underwriting, and effective sales.

New developments arising as a result of the Affordable Care Act are prompting change in this model through such concepts as Accountable Care Organizations, but incentivizing or providing a financial return in healthcare by cost savings, such as provided by the present technology, is in its infancy. Given the potential return of up to $300,000 per patient transplanted as opposed to remaining on dialysis and the fact that there are over 600,000 patients on dialysis, there is perhaps no better opportunity to improve the quality of healthcare while simultaneously reducing its cost than by creating kidney transplants that would not otherwise have occurred.

In 2011, over 115,000 people were diagnosed with end stage renal failure (ESRD) in the United States. While a significant portion of these individuals are not practical candidates for renal transplantation, because of age or infirmity, it is noteworthy that in 2011 only 34,020 patients were added to the kidney transplant waiting list that already contained 86,000 waiting patients. It is likely that there are a significant number of patients remaining on dialysis who could have been transplanted had there been more appropriate management of their ESRD. In 2011, only 17,671 of 86,548 (20%) waiting patients received kidney transplants; of these, 11,835 received a kidney from a deceased donor and 5,772 were given a living donor's kidney. It is estimated that about one third of patients who have a willing living donor will find that their willing donor is not compatible with them. Thus, in 2014, it is likely that over 3,000 ESRD patients will have a willing, but incompatible living donor. Better management of ESRD patients already referred for transplantation using the present approaches such as kidney exchange, could offer the opportunity for a significant proportion of these incompatible pairs to overcome their incompatibility and create the opportunity for an otherwise unattainable living donor kidney transplant.

Referral of ESRD Patients for Renal Transplantation

Referral of patients for kidney transplantation is inconsistent. Nephrologists, who make a living by providing dialysis care for patients with kidney failure, are in the awkward position of losing income if they refer the patient for a successful transplant. A review of the data suggests that trusting timely referral of patients with ESRD to the doctors and companies that make their living by providing dialysis for those patients, does not achieve the optimal result for patients or payers.

In 2011, the last year for which data is available, 115,643 people were diagnosed with ESRD (see the FIGURE). In 2011, 33,564 patients were placed on the waiting list for a kidney transplant. In other words, 28% of the patients initiated onto dialysis in 2011 had been listed for a kidney transplant (see the FIGURE). As verification that these estimations are the best case, the AHRQ in its 2010 National Healthcare Quality Report noted that from 2000 to 2006, the percentage of dialysis patients who were registered on a waiting list for transplantation increased from 14.5% to 17.1%. They averaged the top five performing states to generate a 2006 achievable benchmark goal of 27.3%. The report stated that: "At the current rate of improvement, the benchmark would not be attained overall for almost 24 years."

Even though there are no publications that estimate the percentage of patients who start dialysis each year who should be referred for a kidney transplant, it is valuable to make an educated guess about this as a demonstration of the magnitude of the problem. As noted above, 115,643 patients started dialysis in 2011 and 33,564 patients were listed for a kidney transplant. Assuming 30,000 out of 115,000 new dialysis patients were placed on the waiting list within one year of referral, and that another 15,000 patients were evaluated but not found to be suitable candidates for transplantation, 70,000 patients remain. If one estimates that 50% of these patients were not suitable candidates for transplant evaluation because of age or infirmity, that still leaves 35,000 patients in 2011 who were not referred for a kidney transplant and should have been. Regardless of the different estimations one could make in this regard, the number of patients on a yearly basis who should be referred for a kidney transplant—and are not—is staggering. This present technology provides ways to give these chronic disease patients access to the best health care available for their situation—kidney transplantation—and outlines how developing a new model using a transplant partner (TP) focused on saving money in the delivery of ESRD can provide reinsurance to existing commercial HIPs for the ESRD patients and achieve excellent returns for the TP that produces these results.

Operational Plan

To redesign the referral of ESRD patients for renal transplantation evaluation, the present technology uses a process where a team of healthcare providers with a passion for offering kidney transplantation as an option for the treatment of ESRD is given early access to patients newly diagnosed with ESRD. In so doing, transplant-oriented healthcare providers will give ESRD patients early access to education about the benefit of transplantation and the opportunity for rapid evaluation of their suitability for a kidney transplant. A partnership is formed between the HIP and the TP, where the HIP provides names and contact information to the TP under strict compliance with the Health Insurance Portability and Accountability Act (HIPAA) standards so that the TP can contact patients who have been newly diagnosed with ESRD in an effort to provide more timely access to kidney transplantation.

Those patients chosen for participation in evaluating a method for redesigning the referral process for kidney transplantation are then contacted and an appointment can be made for an initial educational session by phone. Patients can be offered the opportunity to be evaluated for the possibility of undergoing kidney transplantation and any potential living donors can be invited to join them for their evaluation. If financial assistance is required to help with transportation to the transplantation evaluation session, this transportation can be provided as part of the project.

Timely referral of those patients who do not have a willing living donor can be made to transplant centers selected by the transplant referral specialty team. Given expert knowledge of the U.S. transplant system, patients can be referred to transplant centers known to have short deceased donor waiting times and clinical results at or exceeding national norms. By having the transplant referral specialty team choose the transplant centers for referral, all patients can benefit from the knowledge of an informed transplant consumer and not be impacted by geographic factors that may lead to large inequities for waiting times. The value to an uninformed patient becomes evident when one considers that waiting times vary from less than one year to over eight years depending on geographic location.

The advantages of early referral of ESRD patients for kidney transplantation in terms of the quality of healthcare delivered are clear. The average patient who receives a deceased donor kidney transplant will live about 10 years longer than had the same patient remained on dialysis. The longer a patient is treated with dialysis prior to placement on the deceased donor waiting list, the worse their outcome after a kidney transplant. The average waiting time in the U.S. for a deceased person's kidney is 3-5 years (in California the waiting time is 8-10 years), so decreasing the time to referral and listing as well as referral of patients to transplant centers with shorter waiting times will not only improve quality through earlier transplantation, but earlier transplantation will result in better long-term kidney and patient survival. For those patients fortunate to receive compatible living donor kidney transplants, their improved quality comes from a kidney that lasts 16.6 years on average, whereas the average deceased donor's kidney lasts 8.6 years.

Timely referral of patients with incompatible donors to a kidney paired donation program is another improvement in the quality of healthcare delivered. Given that 4,600 patients per year die while wait-listed for a kidney transplant, the number of lives that can be saved among those tens of thousands of patients not even referred for transplantation, but for whom a living donor is available, is significant. Additional added value can come from the referral of patients by transplant specialists who can help patients select transplant centers whose areas of specialization accommodates the specific needs of older patients or patients with unique problems that would be acceptable to only a small subset of available transplant centers.

Redesigning the referral and evaluation of patients with ESRD and their willing, living donors for possible kidney transplantation/living kidney donation can yield benefits not only from reducing the time from diagnosis to referral, but also from referral to completion of the evaluation and from successful completion of the evaluation to successful kidney transplantation. All patients who develop ESRD can have equal access to the best treatment for ESRD—kidney transplantation—regardless of their geography, socioeconomic status, education level or ethnicity.

Improvements in Quality, Cost, and Access by More Timely Referral

A deceased donor kidney transplant extends the recipient's life by an average of 7.2 years. Accounting for the cost of the extra years of life, a living unrelated kidney donor transplant reduces the lifetime medical costs of the recipient by an average of $94,579. Thus, even though a kidney transplant extends the life of the recipient, total lifetime medical costs are reduced. From a cost effectiveness perspective, in which society would be willing to pay for the survival and quality of life benefits provided by a kidney, it is estimated that living unrelated donor kidney transplants are worth at least $269,000 to society and may be worth as much as $500,000.

Determining the cost of dialysis versus renal transplantation is not straightforward. Non-renal diseases and their associated costs are exacerbated by ESRD, but these expenses are not well captured. Nonetheless, an estimate of these expenses is necessary if one is to calculate a cost-to-benefit ratio that can be obtained by the present technology. As an estimate of the value that could be produced by redesigning the referral of ESRD patients for a given HIP, assume that the HIP has 1,000,000 covered lives and will be responsible for paying for the management of any patients diagnosed with ESRD for 33 months until transferred to the Medicare ESRD program (see Table 2 below). Additional assumptions include an incident of ESRD of 389 per million (the 2011 incidence rate in Southern California) and at the cost for a patient undergoing a preemptive renal transplantation will be $200,000 over 33 months ($100,000 for the renal transplant and $100,000 for immunosuppressive medications), whereas 33 months of hemodialysis care will cost $500,000 per patient.

To determine the current referral rates achieved by the HIP for patients with ESRD, assume that 60% of patients will be eligible for renal transplantation and that 70% of those eligible patients will be referred for a kidney transplant. Thus 233 patients would be referred for transplantation and 163 patients would be referred under the current system. Of the referred patients, assume that 50% will have a willing, living kidney donor, that only two-thirds of these donors will be found to be suitable candidates for kidney donation following evaluation. In this estimation, 61 patients will have medically suitable, willing living kidney donors, but only two-thirds of these (41) will be compatible, leaving 20 candidates with willing, but incompatible living donors. Thus, a total of 103 patients without potential living donors and 20 patients with willing, but incompatible donors will be placed on the deceased donor kidney transplant waiting list (123 total), while 41 patients will be transplanted with a living donor's kidney. Of those patients with willing living donors, it is assumed that 10% will be transplanted preemptively and in the first year after wait-listing, it is assumed that 1% will be transplanted (given a waiting time in California of 8-10 years for a deceased donor's kidney). Thus, in year 1, it is assumed that a total of 42 patients will be transplanted. In year 2, an additional 3 (2.5%) patients will be transplanted and in year 3, 6 (5%) additional patients will be transplanted with a deceased donor's kidney. In total, 51 patients will have been transplanted; appropriately accounting for the reduced cost of dialysis for patients transplanted, 38 patients will have required one year of dialysis, and 5 will have required two years of dialysis. Overall 341 patients required 33 months of dialysis. As seen in Table 2, the total cost for managing the patients from a population of 1,000,000 lives that develop ESRD in the first year of management and caring for them for 33 months until they become Medicare-eligible is $188 million.

TABLE 2

|  | Current Model | Cost | Redesign | Cost |
|---|---|---|---|---|
| Covered Lives | 1000000 |  | 1000000 |  |
| Incidence | 389/1,000,000 |  | 389/1,000,000 |  |
| ESRD for Co | 389 |  | 389 |  |
| Cost for Txp | 100,000 |  | 100,000 |  |
| Cost for Meds | 100,000 |  | 100,000 |  |
| Cost for Dialysis | 500,000 |  | 500,000 |  |
| Savings per Txp | 300,000 |  | 300,000 |  |
| Cost for RTT | 0 |  | 0 |  |
| Eligbile for Txp | 60% |  | 60% |  |
| Referred for Txp | 70% |  | 95% |  |
| Eligbile for Txp | 233.4 |  | 233.4 |  |
| Referred for Txp | 163.4 |  | 221.7 |  |
| With willing LD | 81.7 |  | 110.9 |  |
| Suitable LD | 61.3 |  | 83.1 |  |
| Compatible | 40.9 |  | 55.5 |  |
| Incompatible | 20.4 |  | 27.7 |  |
| Waitlisted | 122.5 |  | 166.3 |  |

TABLE 2-continued

|  | Current Model | Cost | Redesign | Cost |
|---|---|---|---|---|
| Trasplant year 1 | 42.1 | $ 8,418,114 | 77.6 | $ 15,524,980 |
| Trasplant year 2 | 3.1 | $ 529,040 | 36.0 | $ 6,222,122 |
| Trasplant year 3 | 6.1 | $ 417,663 | 49.9 | $ 4,912,201 |
| Total Transplanted | 51.3 |  | 163.5 |  |
| WL after 33 months | 337.7 |  | 225.5 |  |
| Pre-emptive transplants | 6.1 | $ 0 | 41.6 | $ 0 |
| Dialyzed 1 year | 37.5 | $ 6,817,318 | 54.1 | $ 9,829,442 |
| Dialyzed 2 years | 4.6 | $ 1,670,653 | 43.0 | $ 15,618,863 |
| Dialyzed 3 years | 340.8 | $170,391,851 | 250.4 | $125,205,910 |
| Total Cost | 389 | $188,244,640 | 389 | $177,313,519 |
| Savings over 3 years |  |  | $10,931,122 |  |
| Percent Savings |  |  | 5.8% |  |

By redesigning the referral of newly developed ESRD patients, it is assumed that the present technology can achieve the following differences from the status quo. First, instead of 70% of eligible patients being referred for renal transplant evaluation, it is assumed that 95% can be referred. It is also assumed that 50% of those patients with willing living donors can be preemptively transplanted and that 20% of those with willing but compatible donors can be found a transplant through kidney paired donation or desensitization. It is further assumed that patients without willing, compatible living donors can be listed at transplant centers in other states with shorter waiting times for deceased donor kidneys. All other assumptions remain the same as with the status quo. By achieving these aims by improving referral and management of ESRD patients, it is estimated that the overall cost of managing ESRD patients in a population of 1,000,000 can be reduced by $10.9 Million, or 5.8%.

Redesigning the referral of ESRD patients for kidney transplantation for the HIP covering 1,000,000 lives would lead to 102 additional kidney transplants and more than one thousand additional years of life. Thus, the present technology can save a HIP millions of dollars every year going forward just considering the additional kidney transplants that it could create. There are few treatments where the best treatment is also the least expensive, so it is clear that there is considerable financial justification to society to invest in efforts to expand access to kidney transplantation by redesigning the referral of patients for kidney transplantation.

Commercial Insurance Companies and the Transplant Partner

Commercial Insurance companies have difficulty considering the cost of healthcare in increments longer than one year. Therefore, the TP can manage the investment required in year one to save financial resources and lives over the subsequent 5 years. In addition, the TP can interact with federal and state insurance programs (Medicare and Medicaid) in considering and managing the longitudinal cost of healthcare. Companies that self insure can also interact with the TP due to the fact that such companies are also interested not only in one year of healthcare costs, but the cost of healthcare over longer times, including patient lifetimes.

Reverse Transplant Tourism

Reverse transplant tourism methods and systems relate to international kidney exchange in which an indigent international patient overcomes their financial barrier by receiving a living donor kidney from an American donor who is incompatible with their intended recipient. The intended American recipient overcomes their immunological barrier by receiving a living donor kidney from the indigent foreign patient's intended donor.

There are over 2.5 million people worldwide receiving renal replacement therapy. Assuming three-quarters of these people are in the developed world and one-quarter are in the undeveloped world, that would leave 625,000 people in the undeveloped world on renal replacement therapy. There would be many more who simply die of renal failure without the opportunity for kidney transplantation or dialysis. Even so, assuming that 1% of those in the undeveloped world would participate in such a program, 6,250 transplants could be performed. Given that there were 5,770 living donor kidney transplants in the United States in 2011, Reverse transplant tourism could produce a significant increase in the number of U.S. kidney transplants.

Reverse transplant tourism utilizes kidney exchange, or kidney paired donation (KPD), to overcome barriers to living donor kidney transplantation. The process involves pairs of willing but incompatible living kidney donors and their intended recipients who are matched together to create compatible transplants. Essentially, they swap their donor's kidneys. For example, a patient in the U.S. with kidney failure (a.k.a. end-stage renal disease (ESRD)) has insurance to help cover the costs for transplantation, but the donor is not immunologically compatible. In contrast, an indigent, international patient has a willing compatible living donor, but does not have the financial resources and/or facilities available for the transplant or subsequent immunosuppression. In both these cases the patients have barriers that prevent the transplant from moving forward.

Reverse transplant tourism allows the impoverished or indigent patient to overcome a financial barrier by receiving a living donor kidney from a living kidney donor who was incompatible with their intended recipient and lived in a country where the cost of dialysis was more than the cost of transplantation when averaged over time. The intended recipient from the country where transplantation is to occur accordingly saves enough financial resources for all the stakeholders to allow for the payment of two kidney transplants to avoid dialysis for one patient, the intended recipient also overcomes the immunological barrier by receiving a living donor kidney from the indigent patient's intended donor. The financial aspects of the transplant for the indigent recipient are covered by the savings obtained by eliminating the cost of dialysis for the recipient who lived in a country where the cost of dialysis was more than the cost of transplantation when averaged over time (e.g., dialysis can have at least twice the costs over time compared to transplantation).

Reverse transplant tourism can provide an attractive option versus other transplant scenarios. Instead of waiting for an organ in the U.S., some patients decide to participate in transplantation overseas; this practice is referred to as transplant tourism. One of the most unethical issues surrounding transplant tourism is the recruitment of donors, often involving the black market of organ trading. Reverse transplant tourism transforms this practice, so that instead of Americans traveling overseas to engage in an ethically questionable practice, they stay in the U.S. instead and the indigent international donors and their intended recipients are brought to the U.S. and given U.S.-quality health care. Reverse transplant tourism overcomes both financial and immunological incompatibility obstacles, leading to more kidney transplants for patients of all nationalities and income levels. In addition, these transplants and donor nephrectomies are delivered with the safety and healthcare standards expected from U.S. transplant centers.

Reverse-transplant tourism enables a safe and legal way for an international exchange of human organs. Importation of living donor organs is currently illegal in the United States as part of the effort to prevent commercial organ trafficking. Thus, reverse transplant tourism requires the foreign donor to undergo nephrectomy at a U.S. transplant center approved to provide living donor nephrectomy. The cost for transportation, donation surgery, and 30-day recovery would be covered by private donations. This plan complies with UNOS policy. Furthermore, because there are no restrictions prohibiting living KPD between international transplant centers, and because it is likely that American donors would be unwilling to travel outside of the U.S. for donor nephrectomy, the U.S. transplant center could either export the American donor's kidney across international boundaries or bring the international recipient to the U.S. for transplantation if sufficient philanthropic funding is available. If the international recipient is transplanted in their home country using a shipped kidney, the philanthropy required will be limited to coverage of long-term immunosuppression and follow-up care. However, international transport of a living donor's kidney for transplantation will require cooperation with the appropriate customs agents for secure and sterile travel of the donor organ to the foreign transplant center.

Reverse transplant tourism can also be applied to non-directed donor initiated chains of kidney transplants, in which the indigent donor can serve as a non-directed donor to initiate a chain of kidney transplants that ended with the transplantation of the indigent recipient.

Reverse transplant tourism could also be accomplished if there are no ESRD patients with willing but incompatible donors in the country where the cost of dialysis is more than the cost of transplantation when averaged over time. Under this circumstance, a 2-for-1 form of reverse transplant tourism can be arranged in which the indigent recipient brings two donors to the country where the cost of dialysis is more than the cost of transplantation when averaged over time. The first indigent donor would donate a kidney to a recipient whose transplant provides savings by eliminating the cost of dialysis, and a portion of this savings would be applied to cover the transplant of the second indigent donor's kidney into the indigent recipient in the country where the cost of dialysis is more than the cost of transplantation when averaged over time.

It is noted that unless the National Organ Transplantation Act is changed, reverse transplant tourism may require payment from a third party intermediary rather than directly from the health insurance provider that potentially saves money from the transplant in the country where the cost of dialysis is more than the cost of transplantation when averaged over time. One way to accomplish this is the creation of a nonprofit organization that is provided with unrestricted funding from philanthropy that is used to pay for reverse transplant tourism. In this way, the act of financially covering the reverse transplant tourism would be unlinked from the direct savings achieved on a patient-by-patient basis.

Three examples of methods employing reverse transplant tourism are presented below. In these examples, the indigent donor and recipient are referred to as the international donor and international recipient and the country where the cost of dialysis is more than the cost of transplantation averaged over time is the United States. An International/U.S. nonprofit is used in a financial managing capacity for effecting the transplantations. The International/U.S. nonprofit can be a transplant partner (TP), as described herein.

The first example of reverse transplant tourism contemplates that the international donor comes to the United States. In this case, the international donor comes to the U.S. and all medical costs are borne by the U.S. recipient's insurance company (nephrectomy, shipping of kidney, etc), while all of the international donor's travel, food and lodging costs are borne by the International/U.S. nonprofit established to fund reverse transplant tourism transplants. The international recipient stays international and the cost of transplantation is borne by the international country. The cost of subsequent care is paid for by the international country, supplemented with support from the International/U.S. nonprofit. As an example, if the international recipient's national health insurance pays for inpatient care and drugs, as well as outpatient care, but not outpatient medications, the outpatient immunosuppressive drugs and transportation to and from the transplant clinic/hospital can be provided by the International/U.S. nonprofit. The outpatient clinic visit and inpatient admission expenses will be paid for by the international recipient's national health insurance government. The U.S. donor stays in the U.S. and their kidney is shipped to the international country (the costs for this U.S. donor's nephrectomy and medical costs are borne in part by the international country's government according to what they would normally pay for a living donor's kidney to be removed and the remainder is paid by the International/U.S. nonprofit). The U.S. recipient is transplanted in the U.S. and the costs are borne by their insurance company.

The second example of reverse transplant tourism contemplates that both the international donor and international recipient come to the United States. The international donor comes to the U.S. and all medical costs are borne by the U.S. recipient's insurance company (nephrectomy, shipping of kidney, etc) while all of the international donor's travel, food and lodging costs are borne by the International/U.S. nonprofit. The international recipient comes to the U.S. and cost of transplant is borne by International/U.S. nonprofit. If the country where reverse transplant tourism is to take place is the U.S., indirect relationships with the American Health Insurance Providers, philanthropic organizations, Pharmaceutical Companies, Transplant Providers, the U.S. Federal or State Governments and others can be established to provide funding to the International/U.S. nonprofit so it can offer reverse transplant tourism services.

In particular, the per person per year cost for Medicare ESRD for hemodialysis 2011 (last year of data per the 2013 USRDS Annual Report: average dialysis annual cost is $87,945 whereas average annual renal transplantation cost is $32,922.). Commercial Insurance companies estimate that if they can preemptively transplant a patient with ESRD, that they will save $300,000 to $500,000 compared with dialysis for the 33 months for which they are responsible for dialysis costs before the patient becomes eligible for coverage by Medicare in the 34$^{th}$ month (see Irwin, F. D., Bonagura, A. F., Crawford, S. W. & Foote, M. Kidney paired donation: a payer perspective. Am J Transplant 12, 1388-1391 (2012). Using conservative estimations by using the most recent USRDS numbers for the Medicare cost of hemodialysis and transplantation, and considering that dialysis patients generally survive 5 years on dialysis, and the average waiting time in the U.S. is 3-5 years for a deceased donor kidney, the savings over 5 years would be $273,235 per transplant as compared with staying on dialysis. An alternative analysis of the savings from living kidney donation in the United States can be found in: Matas, A. J. & Schnitzler, M. Payment for living donor (vendor) kidneys: a cost-effectiveness analysis. *Am J Transplant* 4, 216-221 (2004). If the international Recipient's transplant procedure and first year of immunosuppression costs $100,000, approximately $100,000 of the $273,235 savings would be used to pay for the cost of the International patient's transplant and first year of immunosuppression. Rather than having the U.S. government or U.S. Commercial Insurance company pay this directly to the nonprofit for each transplant, an unrestricted donation to the nonprofit that would allow them to pay for reverse transplant tourism expenses in such a way that that there is no clear link between the U.S. recipient of the international donor's kidney's health insurance provider, pharmaceutical provider, transplant provider or other provider with a financial interest in the recipient's transplant, and the payment for the international recipient's transplant. However, for reverse transplant tourism to become sustainable, there may need to be a mechanism in place for the insurance company/pharmaceutical company/transplantation provider/others that benefit from such reverse transplant tourism to help fund the nonprofit that makes it possible as pure philanthropy for reverse transplant tourism will not be sustainable. This strategy of bringing the international recipient to the U.S. seems to increase the risk that the international donor is in some way receiving valuable consideration, and it increases the amount of money that needs to be provided by the International/U.S. nonprofit, this is not the case for the first example presented above. Another issue to consider is whether with the first reverse transplant tourism the international donor and recipient are immunologically compatible and participate in such an exchange or whether they are immunologically incompatible as this would clearly create a paired exchange as described in the Norwood exception to the National Organ Transplant Act (NOTA).

The second example therefore effectively exports U.S. quality transplant care to indigent patients, by importing international patients—in some international situations, there may not be the possibility of transplantation in the home country. The cost of subsequent care for the international recipient is paid for by the international country and supplemented (or completely provided in the absence of an international government assistance program) with support from the International/U.S. nonprofit. In the specific case of this mechanism for reverse transplant tourism with a Mexican transplant recipient, the outpatient immunosuppressive drugs and transportation to and from the transplant clinic/hospital can be provided by the International/U.S. nonprofit. The outpatient clinic visit and inpatient admission expenses can be paid for by the Mexican government.

The U.S. donor stays in the U.S. in the second example and their kidney is shipped to the U.S. transplant center that will be providing the transplant for the international recipient (the costs for this U.S. donor's nephrectomy and medical costs are borne in part or in whole by the International/U.S. nonprofit depending on the amount the home international country or indigent recipient can pay). The U.S. recipient is transplanted in the U.S. and the costs are borne by their insurance company.

The third example of reverse transplant tourism contemplates that the international recipient brings two donors to the United States. Two international donors come to the U.S., where one is referred to as the International Donor for the International Recipient (IDIR) and the other is referred to as the International Donor for the American Recipient (IDAR). In this arrangement, the following parameters can apply. All Americans with incompatible donors have been exhausted or there are no U.S. ESRD patients with incompatible donors left who match the IDIR or there are no U.S. ESRD patients whose incompatible donor can give directly to the International Recipient in a simple, 2-way exchange. The only Americans left who need a kidney transplant are Americans who do not have a willing, but incompatible living donor and are thus waiting for a deceased donor's kidney. To create the savings from transplanting an American that provides the revenue (i.e., justifies a donation by the recipient's insurance company to the International/U.S. nonprofit to fund future reverse transplant tourism transplants) to fund the transplant of the indigent international recipient, one international donor (the IDAR) can transplant an American and thus create the savings that then provides the impetus for insurance companies, the U.S. government (Medicare—CMS), and others to provide the philanthropy to the nonprofit that will pay for the costs associated with such international donors and recipients in a sustainable fashion. A second international donor (the IDIR) will be required to provide the kidney for the international recipient.

As a working example, a father (the IDAR) could give his kidney to an American to create the savings of ~$275,000+ that provides justification for the nonprofit to provide $100,000 of this savings to pay for the costs for the transplantation of the mother's kidney (the IDIR) into her daughter (the international recipient). Philanthropy is required to pay for the initial reverse transplant tourism transplants and subsequent immunosuppression and medical follow-up, but eventually, the American recipient's Health Insurance Provider and others will have to provide unrestricted grants to a third party intermediary that provides funding of reverse transplant tourism for it to be sustainable. As already acknowledged, unless NOTA is further amended, reverse transplant tourism may require a sustainable funding strategy that unlinks the "valuable consideration" to American Health Insurance Providers and others who financially or otherwise benefit from reverse transplant tourism by having these beneficiaries donate money for future RTT transplants instead of paying directly for the actual transplant itself. The IDAR comes to the U.S. and all medical costs are borne by the American recipient's insurance company (nephrectomy, shipping of kidney, etc) while all of the international donor's travel, food and lodging costs are borne by the International/U.S. nonprofit. The IDIR comes to the U.S. and all medical costs are borne by the International/U.S. nonprofit. The international recipient comes to the U.S. and cost of transplant is borne by International/U.S. nonprofit. The International/U.S. nonprofit (e.g., a Transplant Partner) can develop the relationships with the American Insurance companies and the U.S. Federal Government so that they will provide funding to the International/U.S. nonprofit so it can continue to offer these services as explained herein. The cost of subsequent care for the international recipient is paid for by the international country, and supplemented (or completely provided in the absence of international government assistance program) with support from the International/U.S. nonprofit. The American recipient is transplanted in the U.S. and the costs are borne by their insurance company.

Benefits and Advantages

There are several improvements to patient wellbeing, transplant coordination and administration, and the management of financial resources, which are attributable to the present technology. One result is an increased transplant organ supply for U.S. recipients, an especially valuable benefit for hard to match recipients. Another benefit is the philanthropic provision of a transplant for a non-U.S. recipient, whose national and/or personal resources would otherwise foreclose transplantation. In particular, patients with kidney failure in the developing world are given access to renal transplantation and, in certain cases, gain access to U.S.-quality healthcare. U.S. patients with incompatible but willing kidney donors are provided access to a larger pool of potential living kidney donors than is offered to them currently through kidney paired donation programs. Patients without willing, living kidney donors are benefited when patients ahead of them on the waiting list are removed from the waiting list as a result of having been transplanted. There are substantial cost savings to the U.S. healthcare system for several stakeholders, including HIPs, hospitals, and patients. The completion of a single kidney transplant can save Medicare $275,000 as compared to dialysis (and the savings can be greater for commercial insurance patients. The present technology can also reduce transplant tourism and black-market transplant tourism, which can endanger donors and recipients and can provide risks including low organ quality and poor care, among associated legal and ethical issues. For example, instead of non-U.S. kidney donors being offered money through a black market middleman in exchange for one of their kidneys, the present technology provides a legal and ethical exchange of living donor kidneys through kidney-paired donation. In this way, the donors do not receive money for their kidneys, but rather receive a transplant for someone they love. It is well established under U.S. law that KPD transplants, motivated by the desire to enable a loved one's transplant, rather than by a desire for profit, do not violate NOTA and are specifically permitted by the Norwood act.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method for providing a transplantable biological material and transplantation of the biological material, the method including a pool of a plurality of donor-recipient pairs, each donor-recipient pair including a recipient in need of the biological material and a donor willing to provide the biological material to the recipient, the method comprising:

providing and transplanting a first biological material from a first donor to a first recipient, the first donor and the first recipient not from the same donor-recipient pair, the first recipient overcoming a first barrier including an immunological barrier, the first barrier preventing transplantation between the donor-recipient pair of the first recipient; and providing and transplanting a second biological material from a second donor to a second recipient, the second donor and the second recipient not from the same donor-recipient pair, the second recipient overcoming a second barrier including a financial barrier, the financial barrier preventing transplantation between the donor-recipient pair of the second recipient;

wherein a projected cost of care over a period of time for the first recipient is reduced due to the providing and transplanting of the first biological material from the first donor to the first recipient and a saving in the projected cost of care is used to offset a transplant cost for the second recipient, the transplant cost for the second recipient including a cost of transplanting the second biological material from the second donor to the second recipient, thereby providing the first biological material to the first recipient to allow the first recipient to overcome the first barrier including the immunological barrier, and providing the second biological material to the second recipient to allow the second recipient to overcome the second barrier including the financial barrier.

2. The method of claim 1, wherein the second barrier further includes a member selected from the group consisting of: an antibody against an HLA antigen, an antibody linked to organ rejection, a blood type incompatibility, a physiological barrier, a viral incompatibility, a lower prognosis overcome by an improved transplantation match, a transplantation match incompatibility that can be overcome by desensitization, and combinations thereof.

3. The method of claim 1, wherein the first donor is paired with the second recipient and the second donor is paired with the first recipient.

4. The method of claim 1, further comprising:

transplanting a third biological material from a third donor to a third recipient, the third donor and the third recipient not from the same donor-recipient pair, the third recipient overcoming a third barrier.

5. The method of claim 4, wherein the first donor is paired with the third recipient, the second donor is paired with the first recipient, and the third donor is paired with the second recipient.

6. The method of claim 1, further comprising:

transplanting an $n^{th}$ biological material from an $n^{th}$ donor to an $n^{th}$ recipient, the $n^{th}$ donor and the $n^{th}$ recipient not from the same donor-recipient pair, the $n^{th}$ recipient overcoming an $n^{th}$ barrier, wherein n is an integer greater than three.

7. The method of claim 6, wherein the first donor is paired with the $n^{th}$ recipient.

8. The method of claim 1, wherein each of the first biological material and the second biological material includes a member selected from the group consisting of a kidney, liver, lung, pancreas, musculoskeletal graft, bone, tendon, skin, and vein.

9. The method of claim 8, wherein each of the first biological material and the second biological material includes a kidney.

10. The method of claim 1, wherein transplanting the first biological material from the first donor to the first recipient occurs within a first nation and the first recipient is a citizen of the first nation and the second recipient is not a citizen of the first nation.

11. The method of claim 10, wherein the first donor is not a citizen of the first nation.

12. The method of claim 11, wherein the second donor is a citizen of the first nation.

13. The method of claim 11, wherein transplanting the second biological material from the second donor to the second recipient includes removing the second biological material from the second donor within the first nation and inserting the biological material in the second recipient within a second nation.

14. The method of claim 10, wherein the first donor is not a citizen of the first nation and the second recipient is not a citizen of the first nation.

15. The method of claim 14, wherein transplanting the second biological material from the second donor to the second recipient occurs within the first nation.

16. The method of claim 1, wherein the first donor is matched to the first recipient according to a method comprising:
identifying a plurality of 1-way combinations, each 1-way combination including a compatible match between a single donor from a one donor-recipient pair with a single recipient from another donor-recipient pair;
performing a plurality of clinical tests to optimize compatibility of the plurality of 1-way combinations; and
selecting at least one of the plurality of 1-way combinations and performing a transplantation of the biological material from the single donor to the single recipient.

17. The method of claim 1, wherein a transplant partner responsible for a health care cost for transplanting the first biological material from the first donor to the first recipient covers a cost for transplanting the second biological material from the second donor to the second recipient, thereby allowing the second recipient to overcome the second barrier.

18. The method of claim 17, wherein the transplant partner is a member of the group consisting of: a re-insurance company, a consultation company, and a part of a health insurance provider.

19. The method of claim 1, wherein the financial barrier includes the cost of transplanting the second biological material to the second recipient.

20. The method of claim 1, wherein the first donor is indigent.

21. The method of claim 1, wherein the second recipient is indigent.

22. The method of claim 1, wherein the first barrier further includes a member selected from the group consisting of: an antibody against an HLA antigen, another antibody linked to organ rejection, a blood type incompatibility, a physiological barrier, a viral incompatibility, a lower prognosis overcome by an improved transplantation match, a transplantation match incompatibility that can be overcome by desensitization, and combinations thereof.

23. The method of claim 18, wherein the health insurance provider is an insurance company, a self-insured company, or a government provider.

24. A method for providing a transplantable biological material and transplantation of the biological material, the method including a pool of a plurality of donor-recipient pairs, each donor-recipient pair including a recipient in need of the biological material and a donor willing to provide the biological material to the recipient, the method comprising:
providing and transplanting a first biological material from a first donor to a first recipient, the first donor and the first recipient not from the same donor-recipient pair, the first recipient overcoming a first barrier including an immunological barrier, the first barrier preventing transplantation between the donor-recipient pair of the first recipient; and
providing and transplanting a second biological material from a second donor to a second recipient, the second donor and the second recipient not from the same donor-recipient pair, the second recipient overcoming a second barrier including a financial barrier, the financial barrier preventing transplantation between the donor-recipient pair of the second recipient;
wherein the first recipient is a citizen of the first nation and the first donor, the second donor, and second recipient are not citizens of the first nation, a projected cost of care over a period of time for the first recipient is reduced due to the providing and transplanting of the first biological material from the first donor to the first recipient, a reduction in the projected cost of care is used to offset a transplant cost for the second recipient, and the transplant cost for the second recipient includes a cost of transplanting the second biological material from the second donor to the second recipient, thereby providing the first biological material to the first recipient to allow the first recipient to overcome the first barrier including the immunological barrier, and providing the second biological material to the second recipient to allow the second recipient to overcome the second barrier including the financial barrier.

25. A method for providing a transplantable biological material and transplantation of the biological material, the method including a pool of a plurality of donor-recipient pairs, each donor-recipient pair including a recipient in need of the biological material and a donor willing to provide the biological material to the recipient, the method comprising:
providing and transplanting a first biological material from a first donor to a first recipient, the first donor and the first recipient not from the same donor-recipient pair, the first recipient overcoming a first barrier including an immunological barrier, the first barrier preventing transplantation between the donor-recipient pair of the first recipient; and
providing and transplanting a second biological material from a second donor to a second recipient, the second donor and the second recipient not from the same donor-recipient pair, the second recipient overcoming a second barrier including a financial barrier, the financial barrier preventing transplantation between the donor-recipient pair of the second recipient;
wherein a projected cost of care over a period of time for the first recipient is reduced due to the providing and transplanting of the first biological material from the first donor to the first recipient, a saving in the projected cost of care is used to overcome the financial barrier, and a transplant partner responsible for a health care cost for transplanting the first biological material from the first donor to the first recipient covers a cost for transplanting the second biological material from the second donor to the second recipient, thereby providing the first biological material to the first recipient to allow the first recipient to overcome the first barrier including the immunological barrier, and providing the second biological material to the second recipient to allow the second recipient to overcome the second barrier including the financial barrier.

26. The method of claim 25, wherein the transplant partner is a re-insurance company.

27. The method of claim 25, wherein the transplant partner is a consultation company.

28. The method of claim 25, wherein the transplant partner is a part of a health insurance provider.

* * * * *